United States Patent
Kwak et al.

(10) Patent No.: US 9,408,670 B2
(45) Date of Patent: Aug. 9, 2016

(54) SURGICAL INSTRUMENT, SUPPORT EQUIPMENT, AND SURGICAL ROBOT SYSTEM

(71) Applicant: Samsung Electronics Co., Ltd., Suwon (KR)

(72) Inventors: Ho-seong Kwak, Seoul (KR); Hyung-joo Kim, Seongnam (KR); Jong-hwa Won, Seoul (KR); Hyun-do Choi, Yongin (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 327 days.

(21) Appl. No.: 13/900,842

(22) Filed: May 23, 2013

(65) Prior Publication Data

US 2014/0128882 A1 May 8, 2014

(30) Foreign Application Priority Data

Nov. 6, 2012 (KR) ........................ 10-2012-0125086

(51) Int. Cl.
*A61B 34/30* (2016.01)
*A61B 19/00* (2006.01)

(52) U.S. Cl.
CPC .............. *A61B 19/2203* (2013.01); *A61B 34/30* (2016.02); *Y10S 901/02* (2013.01); *Y10S 901/41* (2013.01)

(58) Field of Classification Search
CPC .................. A61B 19/2203; A61B 2019/2234; A61B 2019/2238; A61B 2019/2242; A61B 34/30
USPC ........................................ 606/1, 130; 901/19
See application file for complete search history.

(56) References Cited

U.S. PATENT DOCUMENTS

| | | | |
|---|---|---|---|
| 5,820,623 A | 10/1998 | Ng | |
| 6,110,182 A * | 8/2000 | Mowlai-Ashtiani | 606/130 |
| 6,368,330 B1 * | 4/2002 | Hynes et al. | 606/130 |
| 7,930,065 B2 | 4/2011 | Larkin et al. | |
| 8,029,516 B2 | 10/2011 | Mohr et al. | |
| 2006/0206101 A1 * | 9/2006 | Lee | 606/1 |
| 2006/0270902 A1 | 11/2006 | Igarashi et al. | |
| 2007/0137372 A1 * | 6/2007 | Devengenzo et al. | 74/490.01 |
| 2008/0064927 A1 | 3/2008 | Larkin et al. | |
| 2008/0065101 A1 | 3/2008 | Larkin | |
| 2009/0024142 A1 | 1/2009 | Ruiz Morales | |
| 2009/0247821 A1 | 10/2009 | Rogers | |
| 2010/0069833 A1 * | 3/2010 | Wenderow et al. | 604/95.01 |
| 2010/0234687 A1 * | 9/2010 | Azarbarzin | A61B 17/29 600/201 |
| 2011/0264136 A1 * | 10/2011 | Choi et al. | 606/205 |
| 2012/0116382 A1 | 5/2012 | Ku et al. | |
| 2013/0197535 A1 | 8/2013 | Okada | |

FOREIGN PATENT DOCUMENTS

| | | |
|---|---|---|
| GB | 171015 * | 11/1921 |
| JP | 2006314703 A | 11/2006 |

(Continued)

*Primary Examiner* — Lynsey Crandall
*Assistant Examiner* — Nathan J Jenness
(74) *Attorney, Agent, or Firm* — Harness, Dickey & Pierce, P.L.C.

(57) ABSTRACT

A surgical instrument includes an extension portion having a surgical tool at an end thereof, and a head portion connected to the extension portion and actuating the surgical tool. In the surgical instrument, the extension portion includes a first extension portion connected to the head portion, a second extension portion having an elbow joint portion that is bending-actuated by a rigid rod that is reciprocated in a lengthwise direction by the head portion, and a connection portion connecting the first and second extension portions at an angle.

20 Claims, 15 Drawing Sheets

(56) References Cited

FOREIGN PATENT DOCUMENTS

| JP | 2011172787 A | 9/2011 |
|---|---|---|
| KR | 10-2009-0123151 | 12/2009 |
| KR | 10-2010-0078551 | 7/2010 |
| KR | 10-2010-0078562 | 7/2010 |
| KR | 20110030038 A | 3/2011 |
| KR | 10-2011-0109475 | 10/2011 |
| KR | 10-2011-0127563 | 11/2011 |
| KR | 10-2012-0014758 | 2/2012 |
| KR | 10-2012-0053650 | 5/2012 |

* cited by examiner

SURGICAL INSTRUMENT, SUPPORT EQUIPMENT, AND SURGICAL ROBOT SYSTEM

CROSS-REFERENCE TO RELATED APPLICATIONS

This application claims the benefit of Korean Patent Application No. 10-2012-0125086, filed on Nov. 6, 2012, in the Korean Intellectual Property Office, the disclosure of which is incorporated herein in its entirety by reference.

BACKGROUND

1. Field

One or more embodiments of the present disclosure relates to a surgical instrument, support equipment for supporting the surgical instrument, and a surgical robot system comprising the support instrument and support equipment.

2. Description of the Related Art

Because minimally invasive surgery using a surgical robot has received a great deal of attention in recent years, much research has been performed in this area and associated developments have largely occurred. A surgical robot may include a passive arm that is manually operated at a preparation stage before a surgical operation is performed and an active arm that is operated by a surgeon. The active arm includes a surgical instrument that is inserted, for example, into the abdominal cavity or a joint region of a patient in order correct various medical problems.

For a smooth and efficient surgical operation, the surgical instrument is required to have a high operating force, a large workspace, and a dexterous motion with a high degree of freedom. However, it is difficult to embody such a surgical robot system satisfying the above requirements. In particular, satisfying these requirements is quite difficult for a single port surgical robot system for performing a surgical operation through a single path (opening).

SUMMARY

A surgical instrument that may have a large workspace and a high operating force is provided.

Support equipment that supports the surgical instrument and controls movements of the surgical instrument is provided.

Support equipment that may allow a surgical instrument to move around a remote center of motion (RCM) is provided.

A surgical robot system including the above-described surgical instrument and support equipment is provided.

Additional aspects will be set forth in part in the description which follows and, in part, will be apparent from the description, or may be learned by practice of the presented embodiments.

According to an aspect of the present inventive concept, a surgical instrument includes an extension portion having a surgical tool at an end thereof, and a head portion connected to the extension portion and actuating the surgical tool. In the surgical instrument, the extension portion includes a first extension portion connected to the head portion, a second extension portion having an elbow joint portion that is bending-actuated by a rigid rod that is reciprocated in a lengthwise direction by the head portion, and a connection portion connecting the first and second extension portions at an angle.

The surgical instrument may further include a rigid main rod extending from the head portion toward the first extension portion and reciprocated in a lengthwise direction by a motor, and a flexible rod disposed in the connection portion and having one end portion and other end portion respectively connected to the rigid rod and the main rod, the flexible rod being reciprocated by the main rod, performing a rigid motion in a lengthwise direction, and being able to bend.

The connection portion includes a first guide that is arranged at least one of an inner portion and an outer portion of the flexible rod in a bending direction to guide the flexible rod.

The first guide may be of a roller type and may be supported on the connection portion to be capable of rotating in rolling contact with the flexible rod.

The surgical tool may be actuated by a wire actuation method, and the first guide may divide an inner space of the connection portion into a space where a wire for actuating the surgical tool is arranged and a space where the flexible rod is arranged.

The connection portion may be a second guide that is arranged at least one of opposite sides in a direction perpendicular to the bending direction of the flexible rod to guide the flexible rod.

The elbow joint portion may be rolling actuated.

The elbow joint portion may include a first arm connected to the connection portion, a second arm connected to the first arm to be capable of pivoting around a pitching shaft, and a joint link having one end portion connected to the second arm at a position spaced apart from the pitching shaft of the first arm and the other end portion to which the rigid rod is connected, wherein the second arm is bending actuated with respect to the first arm.

According to another aspect of the present inventive concept, support equipment includes at least one surgical instrument, a base member having an insertion area, and at least one movable member supporting the surgical instrument and installed on the base member to be capable of moving around the insertion area.

The support equipment may further include a rigid main rod extending from the head portion to the first extension portion and being reciprocally actuated by a motor in a lengthwise direction, and a flexible rod disposed at the connection portion, having one end portion and other end portion respectively connected to the actuation rod and the main rod, being reciprocally actuated by the main rod, performing a rigid motion in a lengthwise direction, and being capable of bending.

A first guide may be arranged at least one side of an inner portion and an outer portion of the flexible rod in a bending direction and may guide the flexible rod.

The first guide may be a roller type and may be supported on the connection portion and rotating in rolling contact with the flexible rod.

The elbow joint portion may be rolling actuated.

The elbow joint portion may include a first arm connected to the connection portion, a second arm connected to the first arm to be capable of pivoting around a pitching shaft, and a joint link having one end portion connected to the second arm at a position spaced apart from the pitching shaft of the first arm and the other end portion to which the rigid rod is connected, wherein the second arm is bending actuated with respect to the first arm.

The first extension portion may be connected to a side surface of the head portion facing a movement center axis of the movable member.

The first extension portion may be extended from the head portion toward the movement center axis.

The support equipment may include a pivot member on which the surgical instrument is installed is installed on the movable member to be capable of pivoting around a pivot axis that passes through the insertion area, wherein the movement center axis of the movable member, the pivot axis, and an extension axis of the second extension portion have a single cross point that does not change even when the movable member is moved.

The movable member may include first and second movable members that move around first and second movement center axes, respectively. The pivot member may include first and second pivot members, on which first and second surgical instruments are installed, which are respectively installed on the first and second movable members to be capable of pivoting around first and second pivot axes. The first movement center axis, the first pivot axis, and a first extension axis of the first surgical instrument may cross at a first cross point. A second movement center axis, the second pivot axis, and a second extension axis of the second surgical instrument may cross at a second cross point.

The support equipment may further include an installation portion on which the surgical instrument is installed and which is supported on the pivot member to be capable of elevating in a direction along the extension axis.

According to another aspect of the present inventive concept, a surgical robot system includes at least one support equipment, a position adjustment unit supporting the support equipment and moving the support equipment to be located at an incision portion of a testee, and a control station controlling a surgical instrument, the at least one support equipment, and the position control unit, for a surgical operation.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
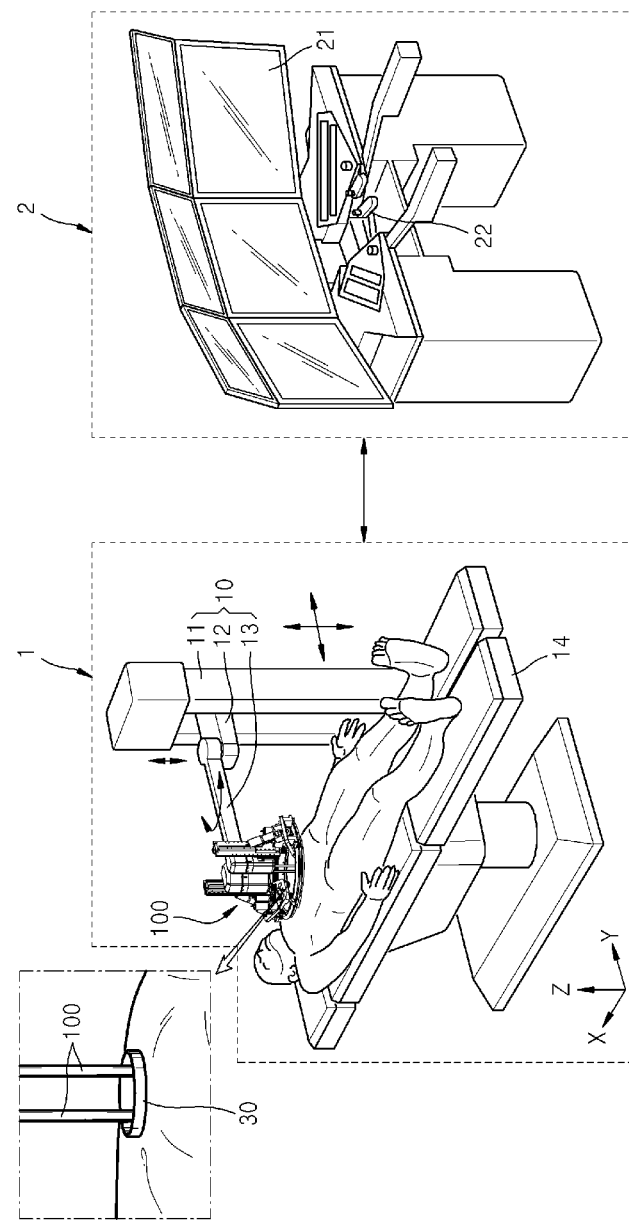
FIG. 1 is a perspective view illustrating the structure of a surgical robot system according to an embodiment of the present inventive concept.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As used herein, the term "and/or" includes any and all combinations of one or more of the associated listed items. Expressions such as "at least one of," when preceding a list of elements, modify the entire list of elements and do not modify the individual elements of the list.

[Surgical Robot System]

FIG. 1 is a perspective view illustrating the structure of a surgical robot system according to an embodiment of the present inventive concept. The surgical robot system of FIG. 1 may be referred to as a surgical manipulation system.

Referring to FIG. 1, the surgical robot system according to the present embodiment is used to perform a surgical operation on a patient by remotely controlling at least one surgical instrument 1000 that is inserted into the patient through an incision portion 30 and observing the inside of the patient through an endoscopic camera image. The surgical robot system may include a surgical station 1 equipped with mechanical apparatuses for performing a surgical operation on the patient and a control station 2 for controlling the surgical station 1.

The surgical station 1 may include support equipment 100 for supporting the surgical instrument 1000 and a positioning unit 10 for locating the support equipment 100 at a desired position, for example, a position corresponding to the incision portion 30 provided in the patient.

For example, the positioning unit 10 may include a vertical column 11 having an elevation block 12 elevating in a vertical direction, that is, in a z-axis direction, and a positioning arm 13 having an end portion where the support equipment 100 is provided. The vertical column 11 may be moved in a horizontal direction, for example, in an x-axis direction and/or y-axis direction. For example, the vertical column 11 may be supported to be able to move in the x-axis direction and/or y-axis direction with respect to an operation table 14 where a testee, such as the patient, lies. Furthermore, the positioning arm 13 may be coupled to the elevation block 12 to be capable of pivoting around, for example, the z-axis. Although FIG. 1 illustrates that two pieces of support equipment 100 are provided at an end portion of the positioning arm 13, the present inventive concept is not limited thereto. For example, if necessary, one or three or more pieces of support equipment 100 may be provided at the end portion of the positioning arm 13.

The control station 2 may include an image display unit 21 for displaying an image that is transferred through an image capturing device, for example, an endoscopic camera, inserted into the patient, and a manipulation unit 22. The manipulation unit 22 controls movements of the positioning unit 10, the support equipment 100, and the surgical instrument 1000, and may include, for example, one or more haptic manipulating devices such as a joystick. An actuating unit for actuating the support equipment 100 and a head portion (1002 of FIG. 2) of the surgical instrument 1000, which is described below, are connected to the control station 2. A surgeon may perform a surgical operation by manipulating the manipulation unit 22 to actuate the support equipment 100 and the surgical instrument 1000. Thus, the control station 2 may be referred to as an operating apparatus for controlling operations of mechanical equipment of the surgical station 1.

[Instrument]

Figure 2:
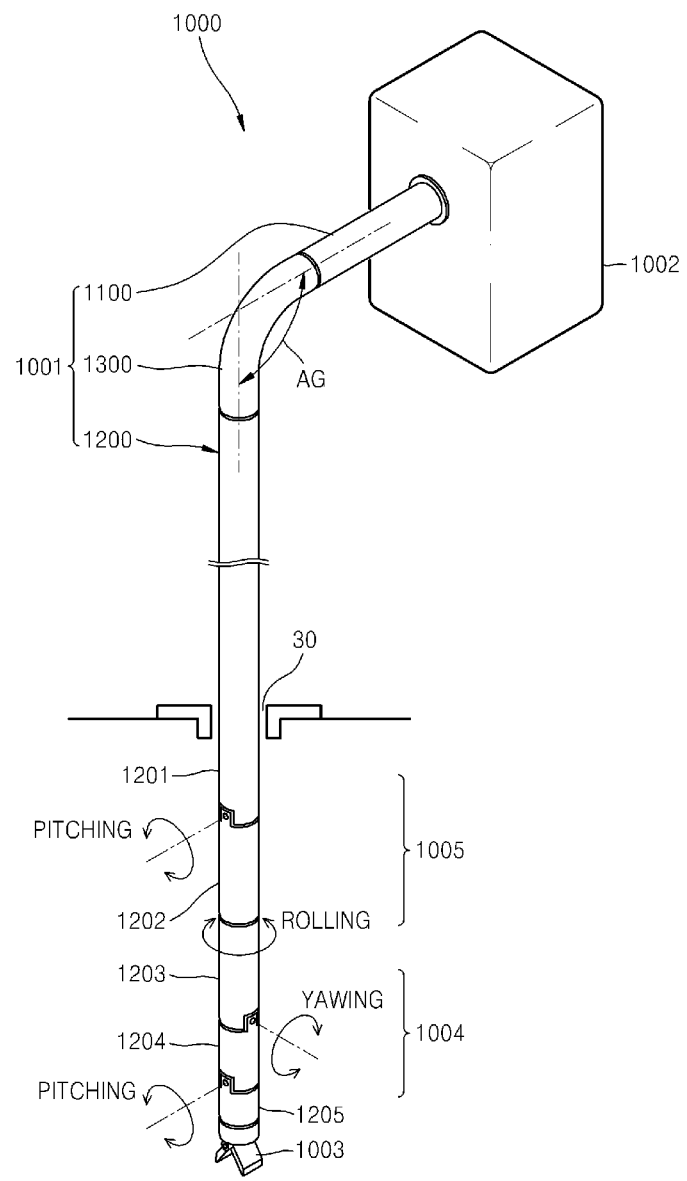
FIG. 2 is a perspective view schematically illustrating an example of a surgical instrument according to an embodiment of the present inventive concept.

FIG. 2 is a perspective view schematically illustrating an example of the surgical instrument 1000 according to an embodiment of the present inventive concept. Referring to FIG. 2, the surgical instrument 1000 may include an extension portion 1001 and a head portion 1002. The extension portion 1001 may have a shape of a long rod and may be inserted into, for example, the abdominal cavity or a joint region of a patient to approach an affected part. A surgical tool 1003 for performing a detailed surgical operation such as an incision or suture via manipulation of a surgeon is provided at an end portion of the extension portion 1001. The surgical tool 1003 may include, for example, a surgical knife, surgical forceps, surgical scissors, cautery (a tool for burning or cutting an affected part by using electric energy or thermal energy), an endoscopic camera, etc.

The extension portion 1001 may be provided with at least one joint portion having at least one degree of freedom so as to perform various surgical operations. For example, the joint portion may include a wrist joint portion 1004 adjacent to the surgical tool 1003 and an elbow joint portion 1005 spaced apart from the wrist joint portion 1004. The wrist joint portion 1004 may be a joint portion capable of, for example, pitching and/or yawing. The elbow joint portion 1005 may be a joint portion capable of, for example, pitching (or yawing) and/or rolling. The head portion 1002 is provided with an actuation unit for actuating the wrist joint portion 1004, the elbow joint portion 1006, and the surgical tool 1003.

The extension portion 1001 includes a first extension portion 1100 connected to the head portion 1002, a second extension portion 1200 having an end portion where the surgical tool 1003 is provided, and a connection portion 1300 connecting the first and second extension portions 1100 and 1200 forming an angle AG therebetween. The elbow joint portion 1005 and the wrist joint portion 1004 are sequentially provided at the second extension portion 1200. The surgical tool 1003 is provided at an end portion of the wrist joint portion 1004. The second extension portion 1200 may include a first arm 1201 connected to the connection portion 1300, a second arm 1202 connected to the first arm 1201 to be capable of pitching (or yawing), and a third arm 1203 connected to the second arm 1202 to be capable of rolling. The first through third arms 1201, 1202, and 1203 form the elbow joint portion 1005. Also, the second extension portion 1200 further includes a fourth arm 1204 connected to the third arm 1203 to be capable of yawing and a fifth arm 1205 connected to the fourth arm 1204 to be capable of pitching. The third through fifth arms 1203, 1204, and 1205 form the wrist joint portion 1004. The surgical tool 1003 is provided at an end portion of the fifth arm 1205. The extension portion 1001 may have an inner hollow polygonal or circular shape so that an actuation unit for actuating the elbow joint portion 1005, the wrist joint portion 1004, and the surgical tool 1003, for example, a wire or a rigid rod, which is described below, may pass therethrough.

For bending actuation, that is, pitching or yawing actuation, of the elbow joint portion 1005, a slider-crank actuation structure using a rigid rod instead of a wire is adopted. The actuation structure to slide a rigid rod is advantageous in transferring a large force compared to an actuation structure using a wire. In the following description, pitching and rolling of the elbow joint portion 1005 is discussed.

Figure 3:
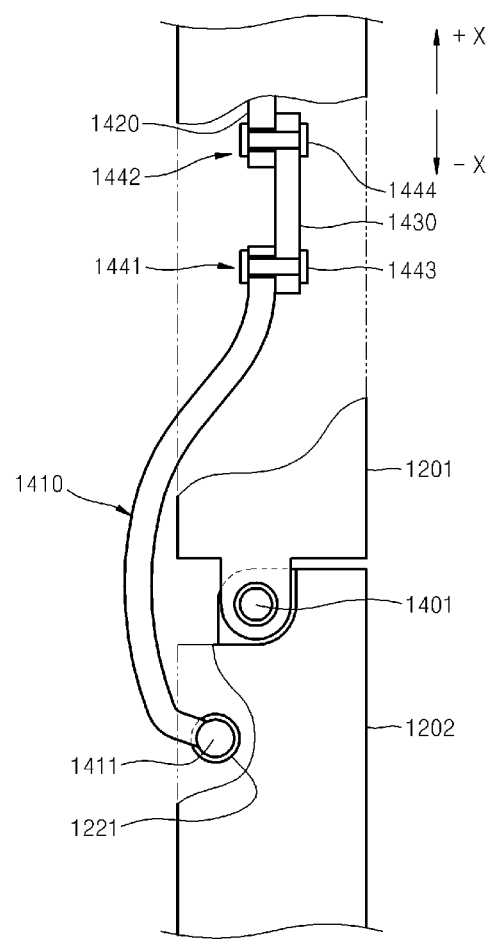
FIG. 3 illustrates an example of a joint structure of an elbow joint portion.

FIG. 3 illustrates an example of a joint structure of the elbow joint portion 1005, according to an embodiment of the present inventive concept. Referring to FIG. 3, the second arm 1202 is connected to the first arm 1201 to be capable of pivoting. For example, a pitching shaft 1401 may be fixed to the first arm 1201 and the second arm 1202 may be pivotably connected to the pitching shaft 1401. Conversely, the pitching shaft 1401 may be fixed to the second arm 1202 and the first arm 1201 may be pivotably connected to the pitching shaft 1401. Also, the first and second arms 1201 and 1202, respectively, may be pivotably connected to the pitching shaft 1401 with a clearance fit. In this case, a stop member (not shown), for example, an E-ring, for preventing the pitching shaft 1401 from deviating in a lengthwise direction thereof, may be coupled to the pitching shaft 1401.

An actuation rod 1420 that is reciprocally actuated in a lengthwise direction is provided at the first arm 1201. A structure of reciprocally actuating the actuation rod 1420 in the lengthwise direction is described below with reference to FIGS. 5A and 5B. A joint link 1410 is actuated by the actuation rod 1420 to allow the second arm 1202 to pivot around the pitching shaft 1401. One end portion of the joint link 1410 is connected to the second arm 1202 and the other end portion thereof is connected to the actuation rod 1420. The joint link 1410 may be connected to the second arm 1202 by, for example, a pin 1411, to be capable of pivoting, for example, in the same direction as a pivot direction of the second arm 1202. For example, the pin 1411 may be fixed to the second arm 1202, and one end portion of the joint link 1410 may be pivotably connected to the pin 1411 in a clearance fit. Alternatively, the pin 1411 may be fixed to the joint link 1410 or integrally formed with the join link 1410, and the pin 1411 is inserted into a through-hole portion 1221 provided in the second arm 1202. In an embodiment, when the pin 1411 is integrally formed with the joint link 1410, the pin 1411 may be integrally formed of single-piece construction of a common material with the joint link 1410. Although it is not illustrated in the drawings, the other end portion of the joint link 1410 may be directly connected to the actuation rod 1420. In this case, the other end portion of the joint link 1410 may be pivotably connected to the actuation rod 1420. The pivotal axis of the joint link 1410 may be, for example, parallel with or perpendicular to the pivotal axis of the second arm 1202. Also, as illustrated in FIG. 3, the other end portion of the joint link 1410 may be connected to the actuation rod 1420 via an intermediate member such as intermediate member 1430. At least one of a first connection portion 1441 between the other end portion of the joint link 1410 and the intermediate member 1430 and a second connection portion 1442 between the intermediate member 1430 and the actuation rod 1420 may have a connection structure that may be capable of pivoting in at least one direction. The pivotal axis of any of the first connection portion 1441 and the second connection portion 1442 may be, for example, parallel with or perpendicular to the pivotal axis of the second arm 1202. In the present embodiment, each of the first and second connection portions 1441 and 1442 may have a connection structure that is capable of pivoting. The first connection portion 1441 that is capable of pivoting may have, for example, a structure in which a pin 1443 provided at the intermediate member 1430 is inserted in a through hole (not shown) provided in the other end portion of the joint link 1410 having a diameter greater than that of the pin 1443. The second connection portion 1442 that is capable of pivoting may have, for example, a structure in which a pin 1444 provided at the intermediate member 1430 is inserted in a through hole (not shown) provided in the actuation rod 1420 having a diameter greater than that of the pin 1444.

The joint link 1410 may be an elastic body formed of an elastic material. The elastic material may be a superelastic material. For example, the joint link 1410 may be formed of an elastic material such as a shape memory alloy (SMA). The SMA may be, for example, Ni—Ti, Cu—Zn, Cu—Zn—Al, Cu—Al—Ni, etc. The shape of the joint link 1410 need not be particularly restricted. The cross-sectional shape of the joint link 1410 may be constant and, in some cases, may be non-constant, that is variable or irregular, such that a large amount of deformation may occur in a particular portion. The joint link 1410 may be a non-elastic body. In this case, the intermediate member 1430 may be formed of an elastic material such as a leaf spring.

The distance between the pin 1411 and the pitching shaft 1401 may be greater than the diameters of the first and second arms 1201 and 1202. For example, the distance between the pin 1411 and the pitching shaft 1401 may be about 1.5 times or more, or particularly, about 1.5 to 3 times, greater than the diameters of the first and second arms 1201 and 1202. When a force to reciprocate the actuation rod 1420 is determined, a stronger moment may be generated as the distance between the pin 1411 and the pitching shaft 1401 increases. Also, the actuation rod 1420 is a rigid body and may be, for example, a metal rod such as a steel rod having a diameter of, for example, about 2 mm. The joint structure using the actuation rod 1420 formed as a rigid body may transfer a stronger force to a joint compared to a structure using a wire. Thus, by using the surgical instrument 1000, a surgical operation may be performed with a strong force. That is, the actuation rod 1420 may be forcefully actuated.

Figure 4:
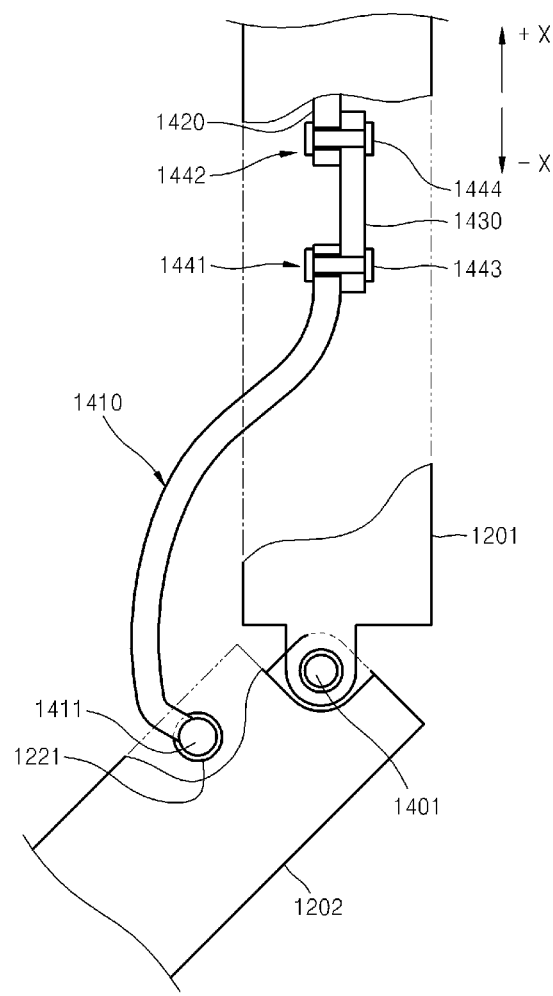
FIG. 4 illustrates a state of a second arm in a pivoting state in the example of a joint structure of an elbow joint portion of FIG. 3.

According to the above-described structure, when the actuation rod 1420 is pulled by an actuator (not shown) in a +X direction of FIG. 3, the pulling force is transferred to the second arm 1202 via the joint link 1410, and thus, the second arm 1202 pivots around the pitching shaft 1401 as illustrated in FIG. 4. Accordingly, the joint link 1410 that is an elastic body is elastically deformed to a certain degree and may absorb a bending stress applied to a connection portion between the joint link 1410 and the actuation rod 1420. When the joint link 1410 is a non-elastic body, the intermediate member 1430 that is an elastic body is elastically deformed, and thus, a bending stress may be absorbed. In the state of FIG. 4, when the actuation rod 1420 is pushed in a −X direction, the second arm 1202 pivots to reach the state as shown in FIG. 3.

Figure 5A:
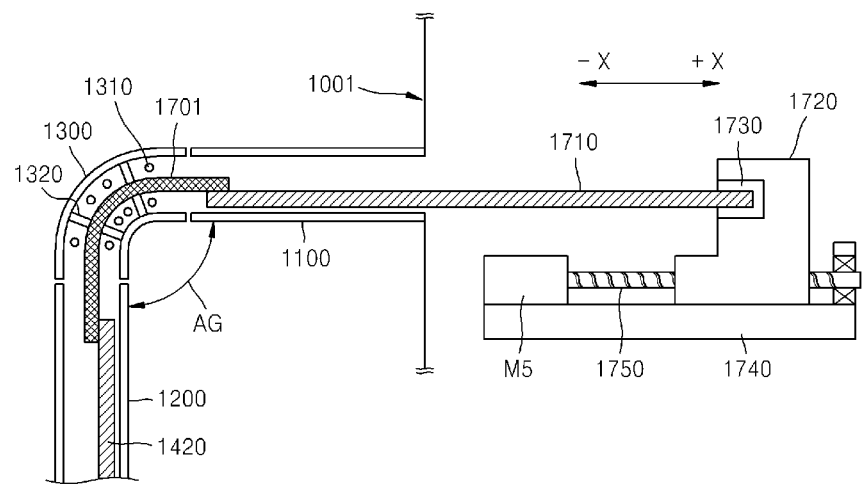
FIG. 5A illustrates an example of an actuation structure to actuate the elbow joint portion of FIG. 3.

FIG. 5A illustrates an example of a rod actuation portion to actuate the actuation rod 1420 to reciprocate in a lengthwise direction. Referring to FIG. 5A, according to the surgical instrument 1000 of the present embodiment, the second extension portion 1200 is connected to and forms an angle AG with the first extension portion 1100 that is connected to the head portion 1002. To this end, the connection portion 1300 forming the angle AG between the first and second extension portions 1100 and 1200 is provided between the first and second extension portions 1100 and 1200. The actuation rod 1420 that is a rigid body is not bent. Thus, the actuation rod 1420 may not pass through the connection portion 1300.

To address this matter, the actuation rod 1420 is connected to a flexible rod 1701 that can pass through the connection portion 1300, and the flexible rod 1701 is connected to a main rod 1710. The main rod 1710 may be, for example, a metal rod such as a steel rod having a diameter of, for example, about 2 mm, similar to the actuation rod 1420. One end portion of the main rod 1710 is fixed to a mobile block 1720 by a clamp 1730. The mobile block 1720 is supported on a base 1740 to be capable of moving in a lengthwise direction of the main rod 1710. To move the mobile block 1720, a lead screw 1750 rotated by, for example, a motor M5, may be employed. The lead screw 1750 penetrates the mobile block 1720 and is supported on the base 1740. A screw thread to be engaged with a screw portion of the lead screw 1750 is provided on the mobile block 1720.

Figure 5B:
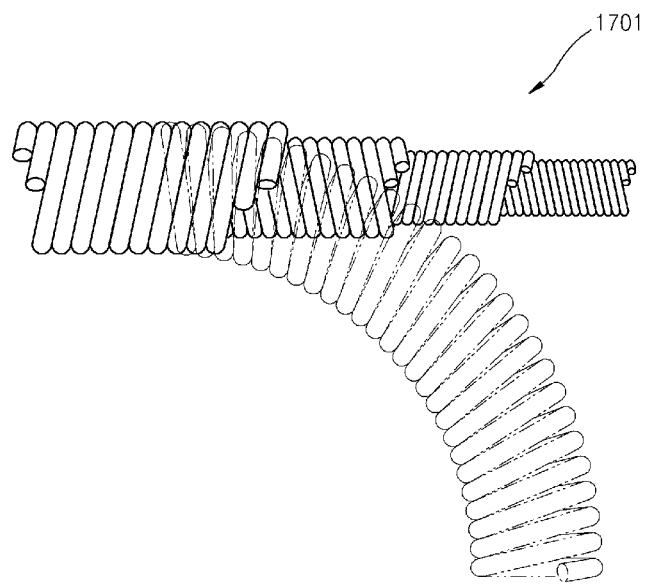
FIG. 5B illustrates an example of a flexible rod.

The flexible rod 1701 is a member that acts like a rigid body in a lengthwise direction and may be flexibly bent within a predetermined angle range. FIG. 5B illustrates an example of the flexible rod 1701. Referring to FIG. 5B, the flexible rod 1701 may have a shape of winding a metallic or steel wire a plurality of times like a coil so as to have flexibility. The steel wire may be a thin spring steel wire. Although FIG. 5B illustrates a steel wire wound in four (4) tiers, the present inventive concept is not limited thereto. Also, the cross-section of the steel wire may be various, for example, rectangular, circular, etc. Further, in FIG. 5B, double spiral steel wires forming respective tiers are wound. However, each tier may be formed by single spiral steel wire or triple or multiple spiral steel wires, if necessary. Although it is not illustrated in FIG. 5B, a jacket may be provided around the outer circumference of the flexible rod 1701. The flexible rod 1701 having the above structure may be bent as indicated by a two-dot-dashed line in FIG. 5B, but may be almost rigid in an axial direction, thereby acting like a rigid body in the axial direction. Thus, the reciprocation motion of the main rod 1710 may be transferred to the actuation rod 1420 via the connection portion 1300 that is bent.

To secure a stroke of the actuation rod 1420 to actuate the elbow joint portion 1005, the length of the flexible rod 1701 may be greater than that of the connection portion 1300. Since the actuation rod 1420 and the main rod 1710 are not able to enter a bent portion of the connection portion 1300, the length of the flexible rod 1710 may be equal to or greater than a sum of the length of the connection portion 1300 and the stroke of the actuation rod 1420. The length of the flexible rod 1701 refers to a length excluding the length for connection between the main rod 1710 and the actuation rod 1420.

The connection between the main rod 1710 and the flexible rod 1701 and the connection between the flexible rod 1701 and the actuation rod 1420 may be achieved by a variety of methods, for example, a clamping method using a clamper, an axis coupling method using a flange, a method using a pin, etc.

In the above-described structure, the mobile block 1720 is moved back and forth by rotating the motor M5, and thus, the main rod 1710 may be reciprocated in the −X and +X directions. A reciprocating actuating force of the main rod 1710 is transferred to the actuation rod 1420 via the flexible rod 1701. Accordingly, the second arm 1202 may be actuated to be bent with respect to the first arm 1201.

Figure 6:
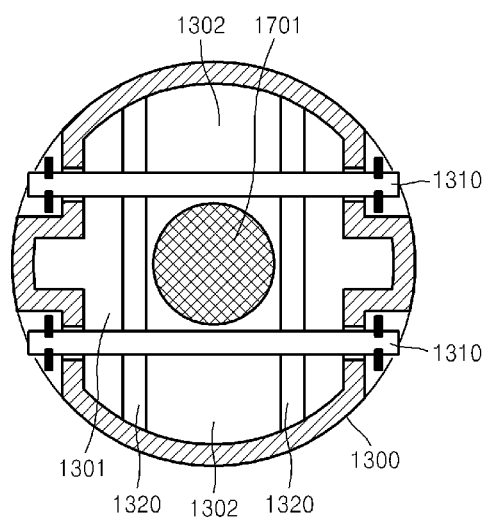
FIG. 6 is a cross-sectional view of a connection portion.

To guide the flexible rod 1701 to be smoothly bent in the connection portion 1300 or at the connection portion between the connection portion 1300 and the first extension portion 1100 or the second extension portion 1200, a guide unit may be provided at the connection portion 1300. The guide unit may be, for example, a plurality of first guides 1310 that cross the connection portion 1300 and are arranged along the lengthwise direction of the flexible rod 1701 as illustrated in FIG. 5A. The first guides 1310 are arranged, for example, at the inner side and/or outer side of the flexible rod 1701 that is bent in the connection portion 1300 to restrict a bending range of the flexile rod 1701. Accordingly, the reciprocal stroke of the main rod 1710 may not be excessively reduced by the bending of the flexible rod 1701. Also, the first guides 1310 may be of a roller type, and are supported on the connection portion 1300 to be capable of rotating in rolling contact with the flexible rod 1701 to guide the smooth reciprocation of the flexible rod 1701 in the lengthwise direction, as illustrated in FIG. 6. Also, the first guides 1310 divides an interior space of the connection portion 1300 into a space 1301 where the flexible rod 1701 is arranged and a space 1302 where wires for actuating the surgical tool 1003 and the wrist joint portion 1004 and a wire for rolling actuating the elbow joint portion 1005, which are described below, pass and thus the wires do not interfere with the flexible rod 1701.

As illustrated in FIGS. 5A, 5B, and 6, the guide unit may further include a plurality of second guides 1320 arranged at one side or opposite sides with respect to a direction perpendicular to the direction in which the flexible rod 1701 is bent, in order to guide the flexible rod 1701. The second guides 1320 like the first guides 1310 may be of a roller type, which are supported on the connection portion 1300 to be capable of rotating in rolling contact with the flexible rod 1701 to guide the smooth reciprocation of the flexible rod 1701 in the lengthwise direction.

Figure 7:
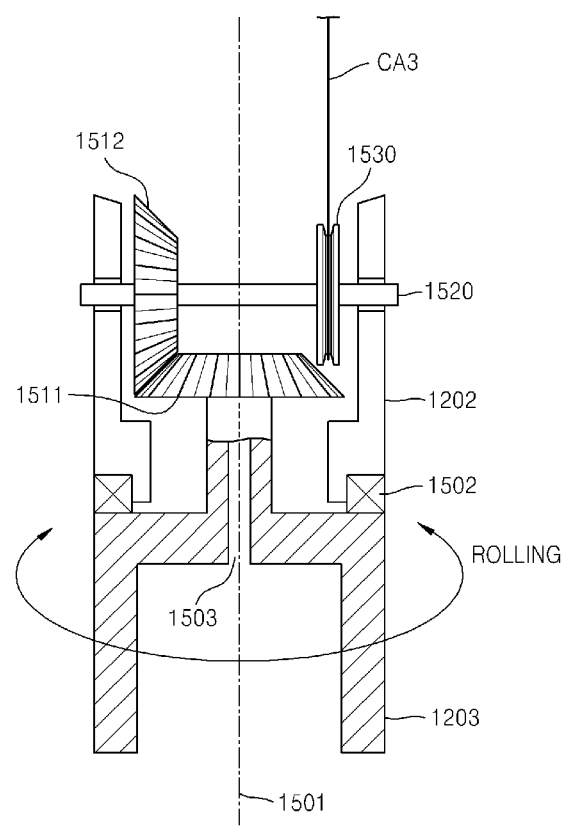
FIG. 7 illustrates an example of a structure for rolling actuation of the elbow joint portion.
Figure 8:
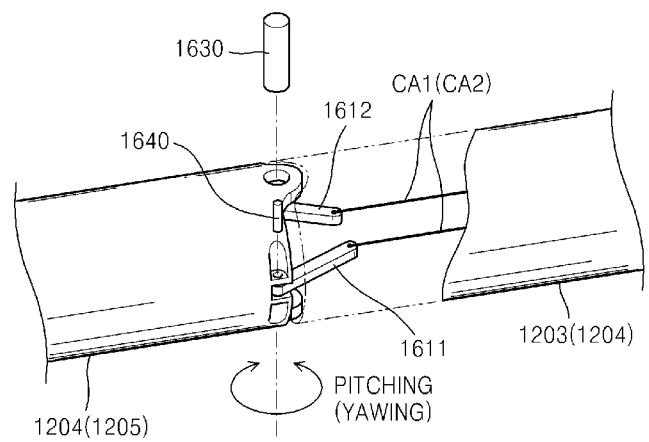
FIG. 8 illustrates an example of a structure for pitching actuation of a wrist joint portion.

The pitching (yawing) actuation of the wrist joint portion 1004 and the rolling actuation of the elbow joint portion 1005 may be actuated by, for example, a well-known actuation method using a wire. Referring to FIGS. 7 and 8, examples of structures for the pitching (yawing) actuation of the wrist joint portion 1004 and the rolling actuation of the elbow joint portion 1005 by using a wire are briefly described below. The actuation structures of FIGS. 7 and 8 are mere examples and the present inventive concept is not limited thereto.

FIG. 7 illustrates an example of a joint structure for rolling. Referring to FIG. 7, a bearing 1502 is interposed between the second arm 1202 and the third arm 1203 and the third arm 1203 is coupled to the second arm 1202 to be capable of pivoting around a rolling axis 1501. A first gear 1511 is provided at an end portion of the third arm 1203 to be coaxially with the rolling axis 1501. A through-hole portion 1503 may be provided in a central portion of the first gear 1511. Wires for actuating the wrist joint portion 1004 and the surgical tool 1003, which are described below, may pass through the throughhole portion 1503. A second gear 1512 engaged with the first gear 1511 is provided at the second arm 1202. The first and second gears 1511 and 1512 may be bevel gears having axes perpendicular to each other. The second gear 1512 is provided at a shaft 1520 rotatably coupled to the second arm 1202. A pulley 1530 is provided at the shaft 1520. A wire CA3 is wound around the pulley 1530. As the wire CA3 is pulled by using an actuator (not illustrated), the pulley 1530 is forwardly or backwardly rotated, and thus, a rotation force is transferred to the first gear 1511 via the second gear 1512. Thus, the third arm 1203 is rotated around the rolling axis 1501. According to the above structure, rolling actuation is possible, and thus, the wrist joint portion 1004 and the surgical tool 1003 may be rolling actuated.

FIG. 8 illustrates an example of a joint structure for pitching the wrist joint portion 1004. Referring to FIG. 8, the fourth arm 1204 may be pivotably coupled to the third arm 1203 by a pivot pin 1630. For example, two link arms 1611 and 1612 may be connected to the fourth arm 1204. One end portion of each of the link arms 1611 and 1612 may be connected to the fourth arm 1204 to be capable of pivoting by a pin 1640. A wire CA1 may be connected to the other end portion of each of the link arms 1611 and 1612. As the wire CA1 is pulled by the actuator in a lengthwise direction, the fourth arm 1204 may be pitching-actuated around the pivot pin 1630.

The structure for yawing actuation is the same as the structure for pitching actuation, except for the direction of an axis. Thus, in FIG. 8, assuming that the third arm 1203 is the fourth arm 1204, the fourth arm 1204 is the fifth arm 1205, and the wire CA1 is the wire CA2, by pulling the wire CA2 in a lengthwise direction, the fifth arm 1205 may be yawing-actuated with respect to the fourth arm 1204.

Figure 9:
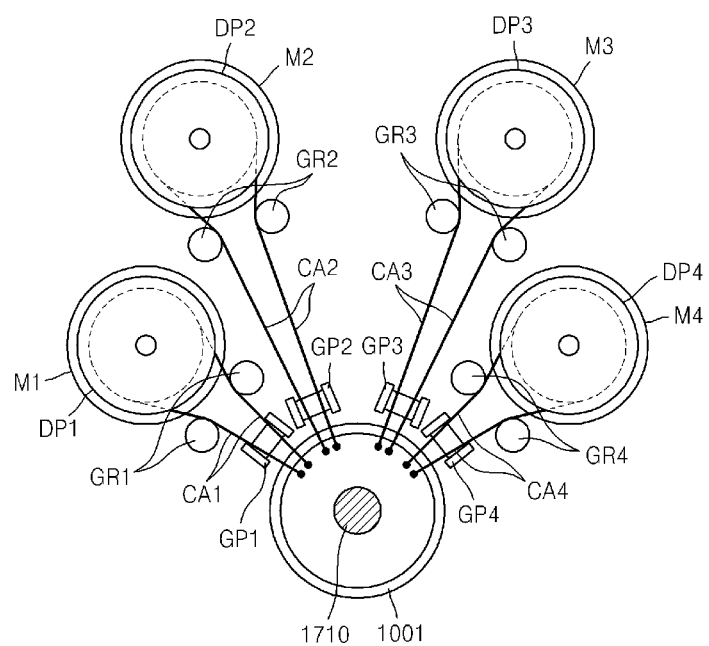
FIG. 9 illustrates an example of a structure for rolling actuation of an elbow joint portion and pitching and yawing actuations of a wrist joint portion by using a wire.

The actuator for actuating a joint using a wire as described above is provided in the head portion 1002. Referring to FIG. 9, the wires CA1, CA2, and CA3 respectively for the pitching and yawing actuations of the wrist joint portion 1004 and the rolling actuation of the elbow joint portion 1005 are illustrated. The wires CA1, CA2, and CA3 may pass through the inside of the extension portion 1001 having a shape of a hollow pipe to be connected to the wrist portion 1004 and the elbow joint portion 1005. Three motors M1, M2, and M3 for respectively actuating the wires CA1, CA2, and CA3 are provided in the head portion 1002. The wires CA1, CA2, and CA3 are guided by guide pulleys GP1, GP2, and GP3 and guide rollers GR1, GR2, and GR3 and are respectively wound around driving pulleys DP1, DP2, and DP3 that are rotated by the motors M1, M2, and M3. In the above structure, pitching, yawing, and rolling actuations are possible by rotating the motors M1, M2, and M3 forwardly and backwardly. A wire CA4, a motor M4, a guide pulley GP4, a guide roller GR4, and a driving pulley DP4 may be used to actuate the surgical tool 1003. The wires CA1, CA2, CA3, and CA4, as described above, may pass through the space 1302 divided by the first guides 1310 and may be connected to the wrist joint portion 1004, the elbow joint portion 1005, and the surgical tool 1003.

When the extension portion 1001 having a partially bent shape is used in the above-described structure, an elbow joint structure using a rigid rod having a strong operating force may be embodied. Thus, a strong operating force and rigidity that are important characteristics required for the surgical instrument 1000 used in conjunction with the surgical robot may be obtained.

Figure 10:
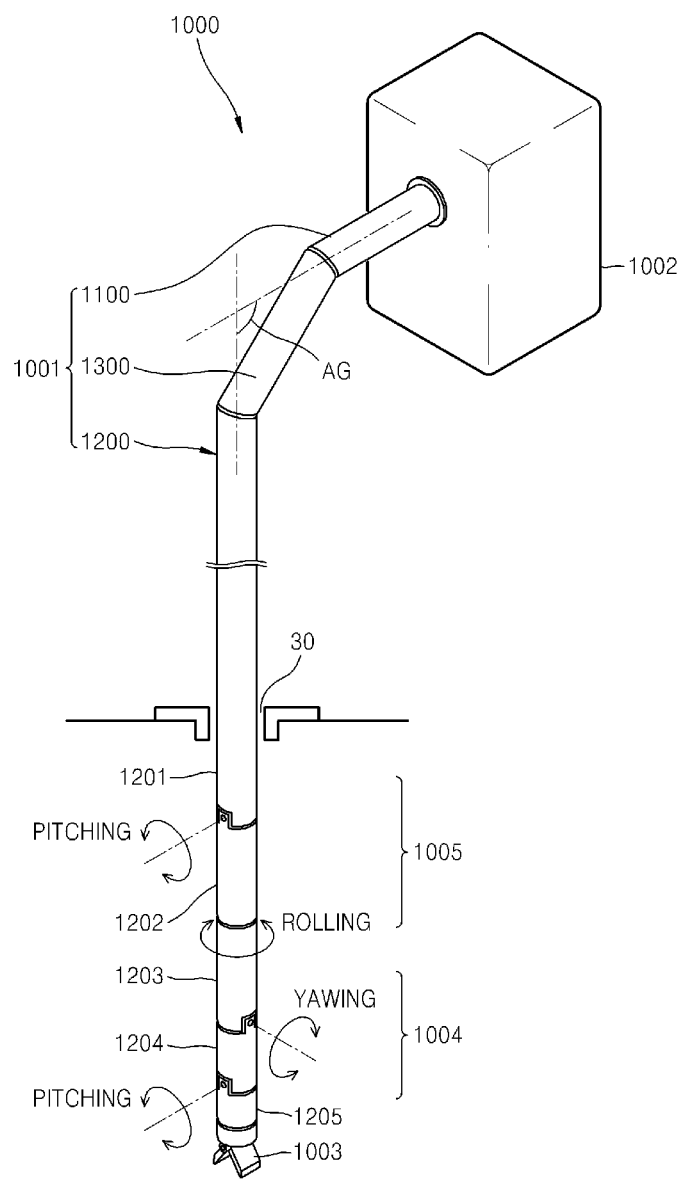
FIG. 10 is a perspective view illustrating an example of a surgical instrument according to another embodiment of the present inventive concept.

Although FIG. 2 illustrates an embodiment in which the connection portion 1300 is bent like a curve, the shape of the connection portion 1300 is not limited to the example of FIG. 2. For example, as illustrated in FIG. 10, the connection portion 1300 may have a linear shape inclined with respect to the first extension portion 1100 and the second extension portion 1200.

[Support Equipment]

Figure 11:
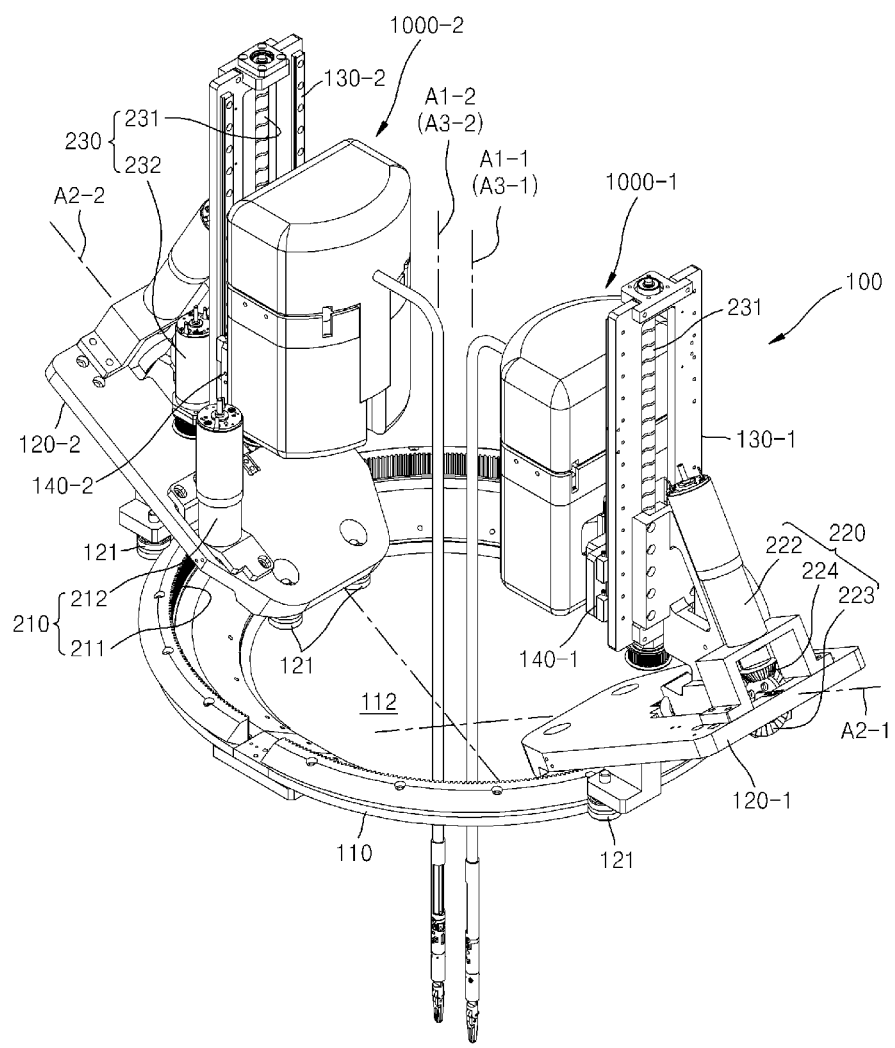
FIG. 11 is a perspective view of support equipment according to an embodiment of the present inventive concept.

FIG. 11 illustrates an example of the support equipment 100 supporting two surgical instruments 1000-1 and 1000-2. Referring to FIG. 11, a base member 110, first and second movable members 120-1 and 120-2, and first and second pivot members 130-1 and 130-2 are illustrated. The first and second movable members 120-1 and 120-2 are installed to be capable of moving around an insertion area 112 that is provided at the base member 110. In an embodiment, the first and second movable members 120-1 and 120-2 are installed to be capable of moving around the insertion area 112 independently of each other. The first and second pivot members 130-1 and 130-2 are pivotably coupled to the first and second movable members 120-1 and 120-2, respectively. First and second installation portions 140-1 and 140-2 may be coupled to the first and second pivot members 130-1 and 130-2 to be capable of elevating in the lengthwise direction of the first and second surgical instruments 1000-1 and 1000-2.

The base member 110 may have a truncated circular conic shape as illustrated in FIG. 11, but the present inventive concept is not limited thereto. The base member 110 may have any shape including the insertion area 112 and capable of guiding the first and second movable members 120-1 and 120-2 to move around the insertion area 112, and the present inventive concept is not limited by a detailed shape thereof. For example, the base member 110 may have a partially truncated circular conic shape, a disc shape having the insertion area 112 at the center portion thereof, or a partially disc shape.

The first and second surgical instruments 1000-1 and 1000-2 are respectively installed at the first and second installation portions 140-1 and 140-2 so that the second extension portion 1200 may pass through the insertion area 112.

The first and second movable members 120-1 and 120-2 are supported on inner and outer circumferential sides of the base member 110 by a plurality of guide rollers 121, and may be moved along the base member 110. A first actuation portion 210 for moving the first and second movable members 120-1 and 120-2 may be a rack and pinion structure. For example, a first drive motor 212 is mounted on each of the first and second movable members 120-1 and 120-2. A pinion (not shown) is coupled to the first drive motor 212. A rack 211 is provided on the base member 110. The rack 211 is formed on the base member 110 in a circumferential direction around a first movement center axis A1-1. In the above structure, as the pinion is rotated by driving the first drive motor 212, the first movable member 120-1 may be moved around the insertion area 112. In other words, the first movable member 120-1 may be moved around the insertion area 112 along a circular movement path around the first movement center axis A1-1. The second movable member 120-2 may be moved around the insertion area 112 along a circular movement path around a second movement center axis A1-2. The structure of the first actuation portion 210 is not limited to the example of FIG. 11. For example, although it is not illustrated in FIG. 11, a linear motor structure may be adopted as the first actuation portion 210.

The first and second pivot members 130-1 and 130-2 may be respectively coupled to the first and second movable members 120-1 and 120-2 to be capable of pivoting around first and second pivot axes A2-1 and A2-2. For example, a pivot shaft (not shown) serving as the first pivot axis A2-1 is provided in the first movable member 120-1 and the pivot member 130-1 may be coupled to the pivot shaft. A second actuation portion 220 for pivoting the first pivot member 130-1 may be embodied by a second drive motor 222 for rotating the pivot shaft. Although it is not illustrated in FIG. 11, a first bevel gear 223 is provided at the pivot shaft and a second bevel gear 224 to engage with the first bevel gear 223 may be provided at the second drive motor 222. In such a structure, as the pivot shaft is rotated by driving the second drive motor 222, the first pivot member 130-1 may pivot around the first pivot axis A2-1. The second pivot member 130-2 may be installed on the second movable member 120-2 to be capable of pivoting around the second pivot axis A2-2 in the same structure. The structure of the second actuation portion 220 is not limited to the example of FIG. 11 and various structures such as a combination of a belt and a pulley instead of a combination of a pair of the bevel gears 223 and 224 may be adopted.

Figure 12:
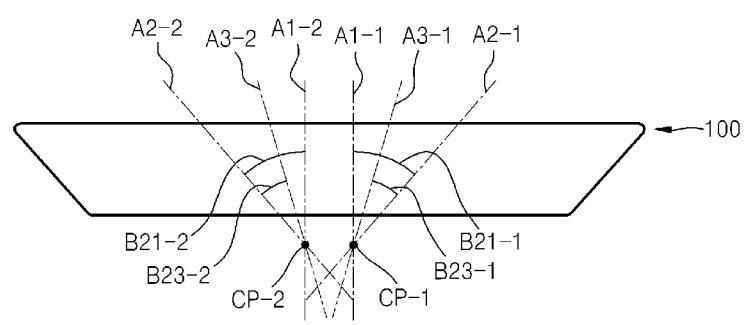
FIG. 12 illustrates an RCM of the support equipment of FIG. 11.

The first and second installation portions 140-1 and 140-2 may be respectively installed at the first and second pivot members 130-1 and 130-2 to be capable of elevating in the directions along first and second extension axes A3-1 and A3-2 of the first and second surgical instruments 1000-1 and 1000-2. Although FIG. 11 illustrates that the first and second movement center axes A1-1 and A1-2 and the first and second extension axes A3-1 and A3-2 are coaxial, the present inventive concept is not limited thereto. As illustrated in FIG. 12, which is described below, the first and second extension axes A3-1 and A3-2 may be respectively inclined with respect to the first and second movement center axes A1-1 and A1-2. A third actuation portion 230 for elevating the first and second installation portions 140-1 and 140-2 may be embodied by using, for example, a lead screw.

Referring to FIG. 11, a lead screw 231 is installed in a direction along the first extension axis A3-1 and the first installation portion 140-1 is installed on the lead screw 231. As the lead screw 231 is rotated by using a third drive motor 232, the first installation portion 140-1 may be elevated in the direction along the first extension axis A3-1. The second installation portion 140-2, having the same structure as the first installation portion 140-1, may be installed on the second pivot member 130-2 to be capable of elevating in the direction of the second extension axis A3-2. The structure of the third actuation portion 230 is not limited to the example of FIG. 11 and various structures such as a structure using a linear actuator may be adopted.

As illustrated in FIG. 12, the first movement center axis A1-1 of the first movement member 120-1, the first pivot axis A2-1 of the first pivot member 130-1, and the first extension axis A3-1 of the first surgical instrument 1000-1 installed on the first pivot member 130-1 have a single first cross point CP-1. Also, the second movement center axis A1-2 of the second movement member 120-2, the second pivot axis A2-2 of the second pivot member 130-2, and the second extension axis A3-2 of the second surgical instrument 1000-2 installed on the second pivot member 130-2 have a single second cross point CP-2. The first and second cross points CP-1 and CP-2 are remote centers of motion (RCM) of the first and second surgical instruments 1000-1 and 1000-2, respectively. The first and second cross points CP-1 and CP-2 may be spaced apart from each other. The interval between the first and second cross points CP-1 and CP-2 may be set to be larger than the diameter of the extension portion 1001 of each of the first and second surgical instruments 1000-1 and 1000-2 to prevent interference between the first and second surgical instruments 1000-1 and 1000-2.

According to the above structure, the first and second surgical instruments 1000-1 and 1000-2 may be moved with respect to the first and second cross points CP-1 and CP-2 as stop points, by respectively moving and pivoting the first and second movable members 120-1 and 120-2 and the first and second pivot members 130-1 and 130-2. Accordingly, the support equipment 100 capable of moving each of the first and second surgical instruments 1000-1 and 1000-2 around the RCM with a 2-degree of freedom may be embodied. Also, as described above, by elevating the first and second installation portions 140-1 and 140-2, the support equipment 100 capable of moving each of the first and second surgical instruments 1000-1 and 1000-2 with a 3-degree of freedom may be embodied. Furthermore, the surgical tool 1003 may have additional 3- or 4-degree of freedom by including the wrist joint portion 1004 and the elbow joint portion 1005. Thus, a dexterous and smooth surgical operation is possible.

According to the support equipment 100 of the present embodiment, the first and second pivot axes A2-1 and A2-2 pass through the insertion area 112. In other words, the first and second pivot axes A2-1 and A2-2 or extension lines thereof pass through the insertion area 112 in the inside of the base member 110 and extend outwardly. According to the above structure, the first and second pivot members 130-1 and 130-2 may be respectively supported on the first and second movable members 120-1 and 120-2 to be capable of pivoting via the simple structure, compared to a conventional surgical robot system in which a surgical instrument is installed at each of a plurality of multi-joint robot arms, as illustrated in FIG. 11.

According to the support equipment 100 of the present embodiment, as illustrated in FIG. 12, assuming that the first pivot axis A2-1 is disposed in a plane including the first pivot axis A2-1 and the first movement center axis A1-1, the first extension axis A3-1 may be disposed between the first pivot axis A2-1 and the first movement center axis A1-1 or may be match the first movement center axis A1-1. In other words, an angle B23-1 between the first pivot axis A2-1 and the first extension axis A3-1 may be the same as or less than an angle B21-1 between the first pivot axis A2-1 and the first movement center axis A1-1. Likewise, assuming that the second pivot axis A2-2 is disposed in a plane including the second pivot axis A2-2 and the second movement center axis A1-2, the second extension axis A3-2 may be disposed between the second pivot axis A2-2 and the second movement center axis A1-2 or may be match the second movement center axis A1-2. In other words, an angle B23-2 between the second pivot axis A2-2 and the second extension axis A3-2 may be equal to or less than an angle B21-2 between the second pivot axis A2-2 and the second movement center axis A1-2. According to the above structure, the interference between the first and second surgical instruments 1000-1 and 1000-2 may be reduced and also workspaces of the first and second surgical instruments 1000-1 and 1000-2 may be increased. Furthermore, by decreasing the angles B23-1 and B23-2 between the first and second pivot axes A2-1 and A2-2 and the first and second extension axes A3-1 and A3-2, a drive load of a drive motor that pivots the first and second pivot members 130-1 and 130-2 may be reduced.

Figure 13:
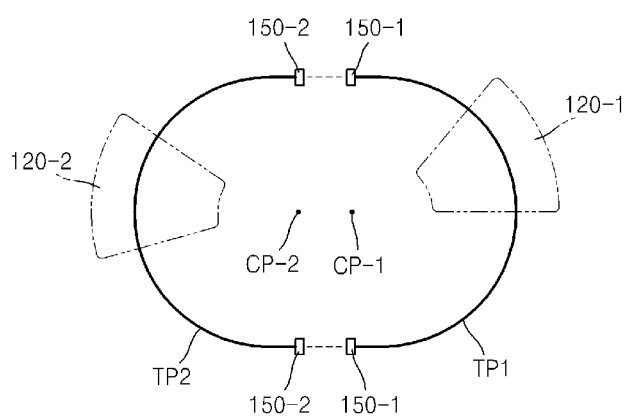
FIG. 13 illustrates movement paths of first and second moving members in the support equipment of FIG. 11.

Referring to FIG. 13, the first movable member 120-1 may move along a first track path TP-1 having an arc shape with the first cross point CP-1 as the center. The second movable member 120-2 may move along a second track path TP-2 having an arc shape with the second cross point CP-2 as the center. The first and second track paths TP-1 and TP-2 do not need to be completely semi-circular shapes. Also, both of the first and second movable members 120-1 and 120-2 may move 360° along the first and second track paths TP-1 and TP-2. In this case, the positions of the first and second cross points CP-1 and CP-2 may be switched with each other, and thus, the first and second surgical instruments 1000-1 and 1000-2 are respectively moved around the second and first cross points CP-2 and CP-1 as RCMs. For example, when the first movable member 120-1 enters the second track path TP-2, the RCM of the first surgical instrument 1000-1 is the second cross point CP-2. However, when both of the first and second movable members 120-1 and 120-2 are disposed at either the first track path TP-1 or the second track path TP-2, the RCMs of the first and second surgical instruments 1000-1 and 1000-2 are matched with each other and thus interference occurs between the first and second surgical instruments 1000-1 and 1000-2. To address the above matter, the movement ranges of the first and second movable members 120-1 and 120-2 may be respectively restricted to the first and second track paths TP-1 and TP-2. A piece of support equipment 100 may further include first and second stop portions 150-1 and 150-2 for stopping the first and second movable members 120-1 and 120-2 from entering the second and first track paths TP-2 and TP-2. For example, the first and second stop portions 150-1 and 150-2 may be protruding portions that protrude from the base member 110 at the opposite end portions of the first and second track paths 120-1 and 120-2 to contact the first and second movable members 120-1 and 120-2.

In a conventional surgical robot system in which a surgical instrument is installed at each of a plurality of multi-joint robot arms, in a process of moving the surgical instrument, the multi-joint robot arms interfere with each other so that it is difficult to secure a large workspace and the surgical instruments may also interfere with each other. In contrast, in the support equipment 100 of the present embodiment that is disposed at a fixed position, the two surgical instruments 1000-1 and 1000-2 may be moved with respect to the RCMs that are space apart from each other. Thus, the first and second surgical instruments 1000-1 and 1000-2 may be moved without interference between the first and second movable members 120-1 and 120-2 and between the first and second pivot members 130-1 and 130-2, and a large workspace may be obtained with respect to each of the first and second surgical instruments 1000-1 and 1000-2. Also, when a plurality of support equipments 100 are arranged at one incision portion 30, no interference occurs between the support equipments 100.

Furthermore, since the support equipment 100 of the present embodiment includes the surgical instrument 1000 having the extension portion 1001 that is partially bent, the movement ranges of the first and second surgical instruments 1000-1 and 1000-2 may be extended in the base member 110 having a given size.

Figure 14:
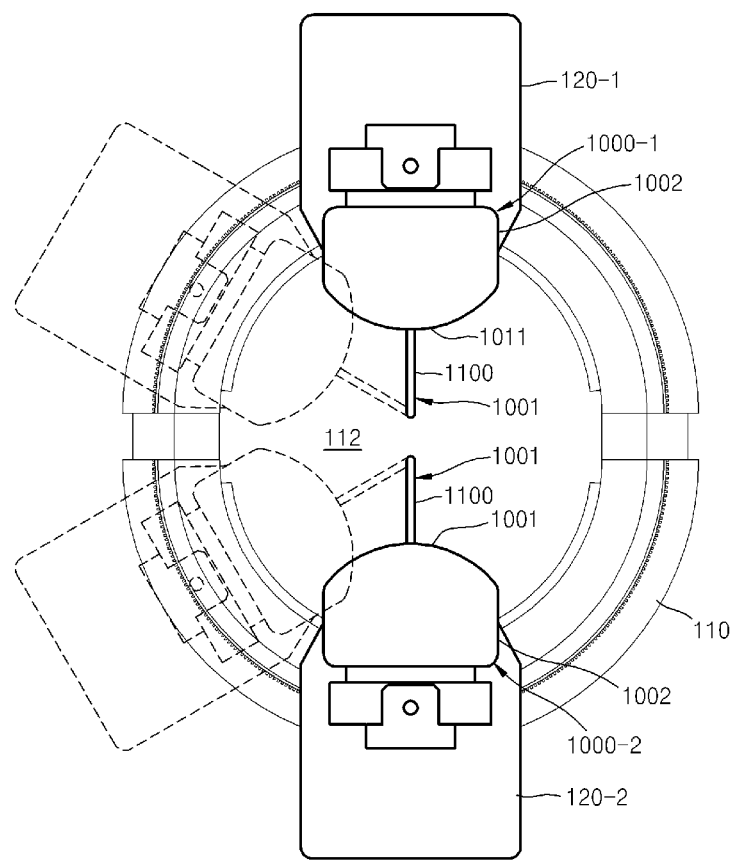
FIG. 14 is a plan view schematically illustrating a movement range of the surgical instrument in the support equipment of FIG. 11.
Figure 15:
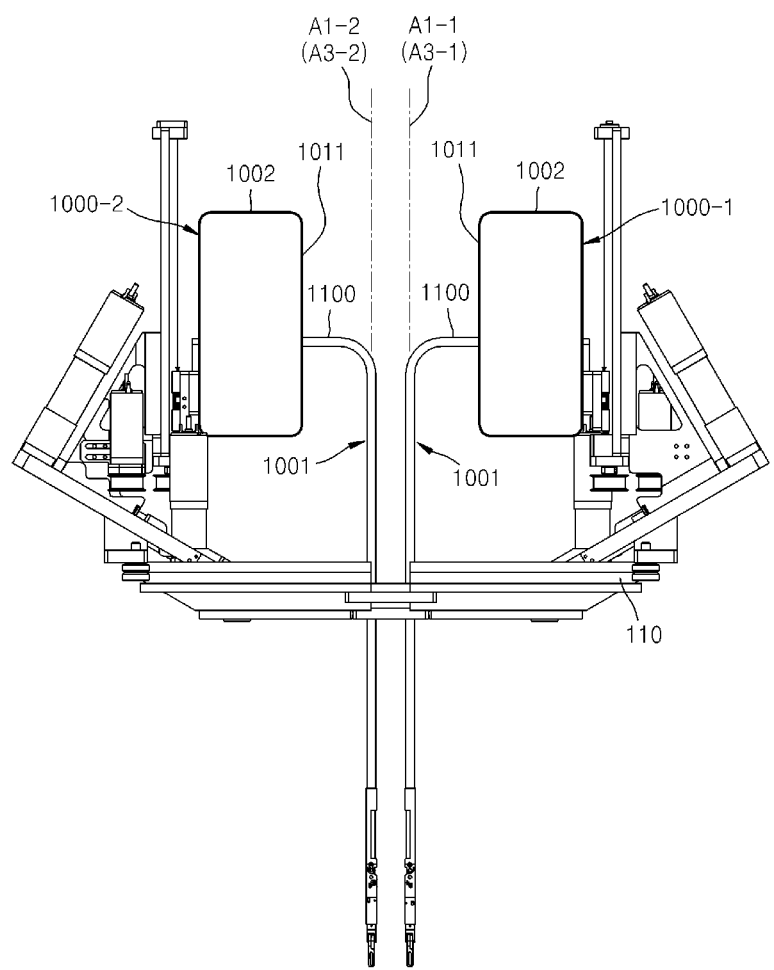
FIG. 15 is side view schematically illustrating a movement range of the surgical instrument in the support equipment of FIG. 11.

FIGS. 14 and 15 are respectively a plan view and a side view schematically illustrating the movement ranges of the first and second surgical instruments 1000-1 and 1000-2. Referring to FIGS. 14 and 15, the extension portion 1001 of each of the first and second surgical instruments 1000-1 and 1000-2 passes through the insertion area 112 of the base member 110. According to the support equipment 100 of the present embodiment, since the extension portion 1001 is bent, even when the extension portion 1001 passes through the insertion area 112, the head portion 1002 may be arranged at a position spaced apart outwardly from the insertion area 112, precisely speaking, from the RCM, by the length of the first extension portion 1100. The extension portion 1001 is coupled to one side surface 1011 of the head portion 1002, that is, to the side surface 1011 facing each of the first and second movement center axes A1-1 and A1-2, and is inwardly extended toward the insertion area 112, that is, toward the first and second movement center axes A1-1 and A1-2 and then extended downwardly therefrom so as to be inserted in the insertion area 112. Thus, the first and second surgical instruments 1000-1 and 1000-2 may be respectively moved across almost overall range of the first and second track paths TP1 and TP2 unless the first and second movable members 120-1 and 120-2 interfere with each other, as illustrated by a dotted line of FIG. 14. In other words, according to the support equipment 100 of the present embodiment, the first and second surgical instruments 1000-1 and 1000-2 may secure a large workspace with substantially no interference.

Figure 16:
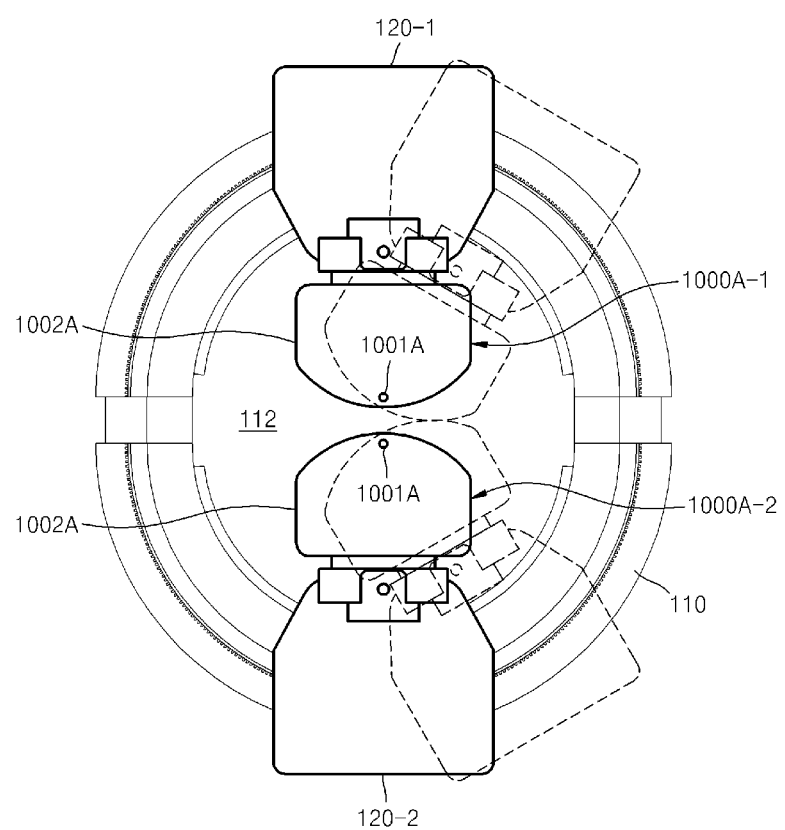
FIG. 16 is a plan view schematically illustrating a movement range of the surgical instrument when the surgical instrument having a linear type extension portion is adopted.
Figure 17:
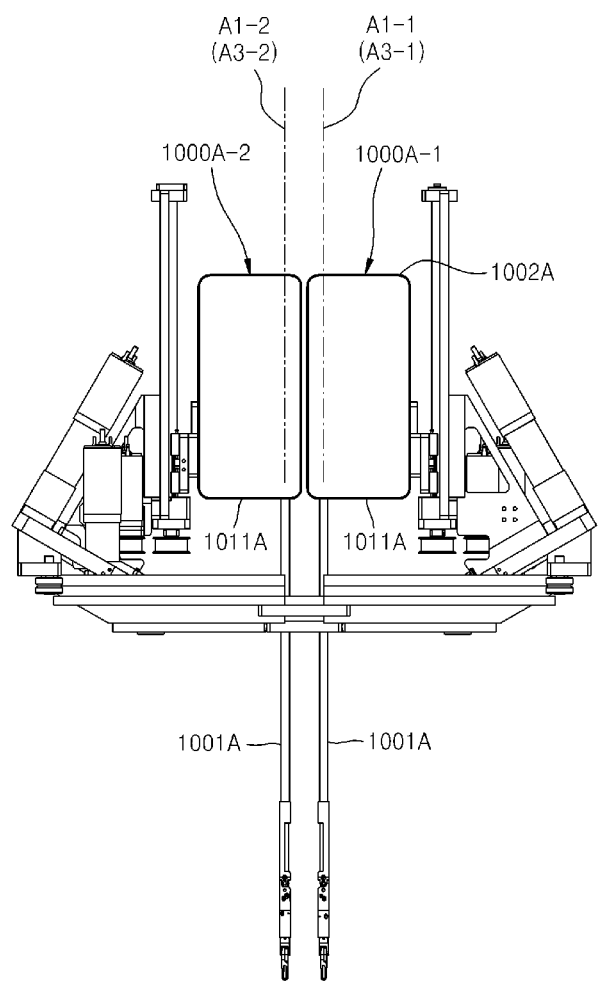
FIG. 17 is a side view schematically illustrating a movement range of the surgical instrument when the surgical instrument having a linear type extension portion is adopted.

In comparison, FIGS. 16 and 17 are respectively a plan view and a side view schematically illustrating movement ranges of two surgical instruments 1000A-1 and 1000A-2 each having a linear type extension portion. Referring to FIGS. 16 and 17, the extension portion 1001A extends downwardly from a low surface 1011A that is perpendicular to the first and second movement center axes A1-1 and A1-2. For the extension portion 1001A to be inserted in the insertion space 112, a head portion 1002A is disposed directly above the insertion area 112. Thus, as indicated by a dotted line of FIG. 16, when the surgical instruments 1000A-1 and 1000A-2 approach each other, the head portions 1002A of the surgical instruments 1000A-1 and 1000A-2 may interference with each other. Thus, there is a range in which the surgical instruments 1000A-1 and 1000A-2 may not move together to avoid interference with each other, and thus, the workspaces of the surgical instruments 1000A-1 and 1000A-2 are reduced.

As described above, according to the support equipment 100 of the present embodiment, by using the surgical instrument 1000 having the bent extension portion 1001, the workspace of the surgical instrument 1000 may be efficiently used and also a large workspace for a surgical operation may be obtained under given conditions.

Although, in the above-described embodiment, a support equipment 100 with two instruments is described, the present inventive concept is not limited thereto. A support equipment in which three or more instruments are installed and each instrument is characterized by an RCM may be embodied.

It should be understood that the exemplary embodiments described therein should be considered in a descriptive sense only and not for purposes of limitation. Descriptions of features or aspects within each embodiment should typically be considered as available for other similar features or aspects in other embodiments. For example, one of ordinary skill in the art may understand that the support equipment, the instrument, and the surgical robot system according to the present inventive concept may be variously modified. Also, the support equipment and the surgical instrument according to the present inventive concept may be applied not only to surgical equipment or system but also to other equipment.

What is claimed is:

1. A surgical instrument comprising:
an extension portion having a surgical tool at an end thereof;
a head portion connected to the extension portion, the head portion configured to generate a reciprocating force; and
a plurality of rods linearly connected from the head portion to the extension portion, the plurality of rods including at least a rigid main rod and a rigid actuation rod connected via a flexible rod such that the rigid main rod is configured to transfer the reciprocating force from the rigid main rod to the rigid actuation rod via the flexible rod, wherein the extension portion includes,
a first extension portion connected to the head portion and having at least a portion of the rigid main rod passing therethrough,
a second extension portion having an elbow joint portion that is bending-actuated by the rigid actuation rod that is reciprocated in a lengthwise direction by the head portion, and
a connection portion connecting the first extension portion and the second extension portion, the connection portion having the flexible rod passing therethrough from the rigid main rod to the rigid actuation rod at an angle, the connection portion having a plurality of guides therein such that the plurality of guides are configured to come into rolling contact with the flexible rod when the flexible rod passes therethrough.

2. The surgical instrument of claim 1; wherein
the rigid main rod is extending from the head portion toward the first extension portion and is reciprocated in a lengthwise direction by a motor, and
the flexible rod is in the connection portion, the flexible rod having one end portion and another end portion each respectively connected to the rigid actuation rod and the rigid main rod, the flexible rod being reciprocated by the rigid main rod, performing a rigid motion in a lengthwise direction, and being capable of bending.

3. The surgical instrument of claim 2, wherein the plurality of guides includes a first guide at least one of an inner portion and an outer portion of the flexible rod in a bending direction to guide the flexible rod.

4. The surgical instrument of claim 3, wherein the first guide is a roller-type guide and is supported on the connection portion to be capable of rotating in rolling contact with the flexible rod.

5. The surgical instrument of claim 3, wherein the surgical tool is actuated by a wire actuation method, and the first guide divides an inner space of the connection portion into a space where a wire for actuating the surgical tool is arranged and a space where the flexible rod is arranged.

6. The surgical instrument of claim 3, wherein the plurality of guides includes a second guide connected to at least two opposite points of the connection portion along a circumference of the connection portion such that the at least two opposite points are in a direction perpendicular to a bending direction of the flexible rod to guide the flexible rod.

7. The surgical instrument of claim 1, wherein the elbow joint portion is rolling actuated.

8. The surgical instrument of claim 1, wherein the elbow joint portion comprises:
a first arm connected to the connection portion,
a second arm connected to the first arm via a pitching shaft, the second arm configured to pivot around the pitching shaft, the second arm being bending actuated with respect to the first arm, and
a joint link having one end portion connected to the second arm at a position spaced apart from the pitching shaft of the first arm and another end portion of the joint link is connected to the rigid actuation rod.

9. A support equipment comprising:
at least one surgical instrument including,
an extension portion having a surgical tool at an end thereof,
a head portion connected to the extension portion, the head portion configured to generate a reciprocating force, and
a plurality of rods linearly connected from the head portion to the extension portion, the plurality of rods including at least a rigid main rod and a rigid actuation rod connected via a flexible rod such that the rigid main rod is configured to transfer the reciprocating force from the rigid main rod to the rigid actuation rod via the flexible rod;
a base member having an insertion area; and
at least one movable member supporting the surgical instrument and installed on the base member to be capable of moving around the insertion area, wherein the extension portion includes,
a first extension portion connected to the head portion and having at least a portion of the rigid main rod passing therethrough,
a second extension portion having an elbow joint portion that is bending-actuated by the rigid actuation rod that is reciprocated in a lengthwise direction by the head portion, and
a connection portion connecting the first extension portion and the second extension portion, the connection portion having the flexible rod passing therethrough from the rigid main rod to the rigid actuation rod at an angle, the connection portion having a plurality of guides therein such that the plurality of guides are configured to come into rolling contact with the flexible rod when the flexible rod passes therethrough.

10. The support equipment of claim 9, wherein
the rigid main rod extending from the head portion to the first extension portion and being reciprocally actuated by a motor in a lengthwise direction, and
the flexible rod at the connection portion having one end portion and another end portion each respectively connected to the rigid actuation rod and the rigid main rod, the flexible rod being reciprocally actuated by the rigid main rod, performing a rigid motion in a lengthwise direction, and being capable of bending.

11. The support equipment of claim 10, wherein the plurality of guides includes a first guide at least one side of an inner portion and an outer portion of the flexible rod in a bending direction, the plurality of guides being configured to guide the flexible rod.

12. The support equipment of claim 11, wherein
the first guide is a roller-type guide, and
the first guide is supported on the connection portion and rotating in rolling contact with the flexible rod.

13. The support equipment of claim 9, wherein the elbow joint portion is rolling actuated.

14. The support equipment of claim 9, wherein the elbow joint portion comprises:
a first arm connected to the connection portion,
a second arm connected to the first arm via a pitching shaft, the second arm configured to pivot around the pitching shaft, the second arm being bending actuated with respect to the first arm, and
a joint link having one end portion connected to the second arm at a position spaced apart from the pitching shaft of the first arm and other end portion connected to the rigid actuation rod connected.

15. The support equipment of claim 9, wherein the first extension portion is connected to a side surface of the head portion facing a movement center axis of the movable member.

16. The support equipment of claim 15, wherein the first extension portion extends from the head portion toward the movement center axis.

17. The support equipment of claim 9, comprising:
a pivot member having the surgical instrument installed thereon, the pivot member being installed on the movable member and configured to pivot around a pivot axis that passes through the insertion area, wherein,
a movement center axis of the movable member, the pivot axis, and an extension axis of the second extension portion have a single cross point that does not change even when the movable member is moved.

18. The support equipment of claim 17, wherein,
the movable member includes a first movable member and a second movable member that move around a respective one of a first movement center axis and a second movement center axis,
the pivot member includes a first pivot member and a second pivot member, on which a first surgical instrument and a second surgical instrument are installed, which are respectively installed on the first movable member and a second movable member, the first pivot member and the second pivot member are configured to pivot around a respective one of a first pivot axis and a second pivot axis,
the first movement center axis, the first pivot axis, and a first extension axis of the first surgical instrument cross at a first cross point, and
the second movement center axis, the second pivot axis, and a second extension axis of the second surgical instrument cross at a second cross point.

19. The support equipment of claim 17, further comprising:
an installation portion having the surgical instrument installed thereon, and the installation portion is supported on the pivot member to be capable of elevating in a direction along the extension axis.

20. A surgical robot system comprising:
at least one support equipment including,
a surgical instrument,
a base member having an insertion area, and
at least one movable member supporting the surgical instrument and installed on the base member to be capable of moving around the insertion area;
a position adjustment unit configured to support the support equipment and move the support equipment to be located at an incision portion of a testee; and
a control station configured to control the surgical instrument, the at least one support equipment, and the position adjustment unit, for a surgical operation, wherein
the surgical instrument includes,
an extension portion having a surgical tool at an end thereof,
a head portion connected to the extension portion, the head portion configured to generate a reciprocating force, and
a plurality of rods linearly connected from the head portion to the extension portion, the plurality of rods including at least a rigid main rod and a rigid actuation rod connected via a flexible rod such that the rigid main rod is configured to transfer the reciprocating force from the rigid main rod to the rigid actuation rod via the flexible rod; and
the extension portion includes,
a first extension portion connected to the head portion and having at least a portion of the rigid main rod passing therethrough,
a second extension portion having an elbow joint portion that is bending-actuated by the rigid actuation rod that is reciprocated in a lengthwise direction by the head portion, and
a connection portion connecting the first extension portion and the second extension portion, the connection portion having the flexible rod passing therethrough from the rigid main rod to the rigid actuation rod at an angle, the connection portion having a plurality of guides therein such that the plurality of guides are configured to come into rolling contact with the flexible rod when the flexible rod passes therethrough.

* * * * *